United States Patent [19]

Aoki et al.

[11] 4,071,633
[45] Jan. 31, 1978

[54] FUNGICIDAL N-TRICHLOROACETYL-N'-CHLOROBENZOYLHYDRAZINE DERIVATIVES

[75] Inventors: Katsumichi Aoki; Susumu Shimizu; Keigo Satake; Shiro Yamazaki; Nobuo Hatakeyama, all of Iwaki, Japan

[73] Assignee: Kureha Kagaku Kogyo Kabushiki Kaisha, Tokyo, Japan

[21] Appl. No.: 772,131

[22] Filed: Feb. 25, 1977

[30] Foreign Application Priority Data

Mar. 2, 1976 Japan .................................. 51-22811

[51] Int. Cl.$^2$ ..................... A01N 9/20; C07C 103/82
[52] U.S. Cl. ................... 424/324; 260/558 H
[58] Field of Search ..................... 260/558 H; 424/324

[56] References Cited

U.S. PATENT DOCUMENTS

| | | | |
|---|---|---|---|
| 3,660,485 | 5/1972 | Cusic et al. | 424/324 X |
| 3,707,477 | 12/1972 | Ost et al. | 260/562 A X |
| 3,884,874 | 5/1975 | Rosenberger et al. | 260/558 H X |
| 4,002,680 | 1/1977 | Brunetti et al. | 260/558 H X |

FOREIGN PATENT DOCUMENTS

| | | |
|---|---|---|
| 22083/68 | 9/1968 | Japan ................................ 260/558 H |
| 12344/66 | 7/1966 | Japan ................................ 260/558 H |
| 49-47528 | 5/1974 | Japan. |
| 49-11061 | 3/1974 | Japan. |

OTHER PUBLICATIONS

Spiegel et al., Chem. Ber. 40, p. 1739.
Konupak et al., CA 55: 12805i (1962).
Mashima, Bull. Chem. Soc. Japan, 35, pp. 332-337.

*Primary Examiner*—Daniel E. Wyman
*Assistant Examiner*—Thomas A. Waltz
*Attorney, Agent, or Firm*—Fleit & Jacobson

[57] ABSTRACT

Novel N-trichloroacetyl-N'-chlorobenzoylhydrazine derivatives, having the following formula:

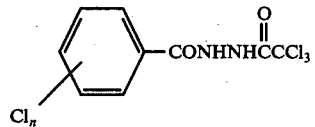

where n stands for 1 or 2, and especially adapted for use as fungicidal agent for agricultural use, and process for manufacturing same.

7 Claims, No Drawings

FUNGICIDAL N-TRICHLOROACETYL-N'-CHLOROBENZOYL-HYDRAZINE DERIVATIVES

BACKGROUND OF THE INVENTION

This invention relates to novel derivatives of N-trichloroacetyl-N'-chlorobenzoylhydrazine, having the following formula (I).

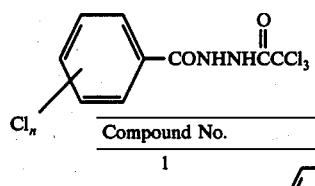

where $n$ stands for 1 or 2, and especially adapted for use as fungicidal agent for agricultural use, and process for manufacturing same.

As N-substituted-N'-chlorobenzoylhydrazine derivatives, hitherto are known N-acetyl-N'-chlorobenzoylhydrazine derivatives, but those of trichloroacetyl-substituted type or more specifically those of the form of N-trichloroacetyl-N'-chlorobenzoylhydrazine are not yet known according to our knowledge.

We have newly synthesized these unknown N-trichloroacetyl-N'-chlorobenzoylhydrazine derivatives, investigated thereinto and found that these novel compounds have highly superior fungicidal effect with respect to various agricultural plant diseases.

It is, therefore, an object of the present invention to provide novel N-trichloroacetyl-N'-benzoylhydrazine derivatives.

A further object is to provide a composition including at least one of the above-mentioned novel compounds as the fungicidally effective substance adapted for the control of agricultural plant diseases.

Still a further object is to provide a process for the preparation of the above group of novel compounds.

The novel derivatives of the above kind may be grouped as shown in the following Table I.

Table I

| Compound No. | Structural Formula | Naming | M.P. | Yield* |
|---|---|---|---|---|
| 1 | (2-Cl phenyl)-CONHNHCOCCl₃ | N-trichloroacetyl-N'-2-chlorobenzoylhydrazine | 168 – 170° C | 57% |
| 2 | (3-Cl phenyl)-CONHNHCOCCl₃ | N-trichloroacetyl-N'-3-chlorobenzoylhydrazine | 143 – 144° C | 76% |
| 3 | (4-Cl phenyl)-CONHNHCOCCl₃ | N-trichloroacetyl-N'-4-chlorobenzoylhydrazine | 165 – 166° C | 70% |
| 4 | (2,4-diCl phenyl)-CONHNHCOCCl₃ | N-trichloroacetyl-N'-2,4-dichlorobenzoylhydrazine | 149 – 150° C | 80% |
| 5 | (2,5-diCl phenyl)-CONHNHCOCCl₃ | N-trichloroacetyl-N'-2,5-dichlorobenzoylhydrazine | 127 – 130° C | 51% |
| 6 | (3,4-diCl phenyl)-CONHNHCOCCl₃ | N-trichloroacetyl-N'-3,4-dichlorobenzoylhydrazine | 183 – 185° C | 50% |

For the preparation of the said novel derivatives, the following steps may be employed:

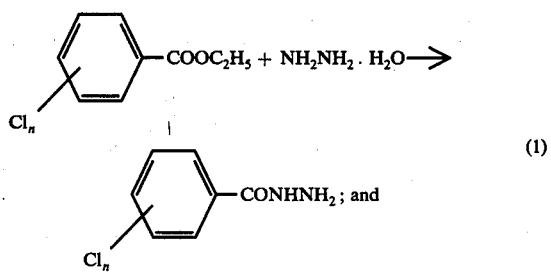

-continued

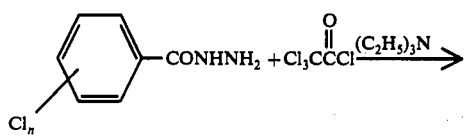

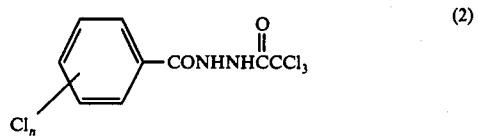

(where n stands for an integer of 1 or 2)

More specifically, chloro-substituted benzoic ester of the above formula (1) and hydrazine hydrate are agitated and heated in a solvent such as alcohol to provide a corresponding acid hydrazide which is then added in a benzene phase, droppingly with equimolar amount of trichloroacetylchloride in the presence of equimolar amount of triethylamine and then the reaction mixture is agitated at room temperature for 1-7 hours to provide the desired final product.

In the following, the above preparing process will be described more in detail with reference to several preferred numerical examples.

EXAMPLE 1

Preparation of N-trichloroacetyl-N'-3-chlorobenzoylhydrazine (Compound No. 2)

29.7g (0.16 mol) of 3-chlorobenzoic ester and 8.9g (0.18 mol) of 100%-hydrazine hydrate in 30 ml of ethanol were refluxed for 3 hours under heat and agitation. Upon cooled down, the thus formed white crystals were filtered and enough washed with ethyl ether. In this way, 13.0g of 3-chlorobenzoic acid hydrazide were obtained in white crystals. m.p.: 156°-158° C. Yield: 48%.

3.4g (0.02 mol) of the hydrazide were suspended in benzene, 100 ml, and added with 2.0g (0.02 mol) of triethylamine and further droppingly with 3.7g (0.02 mol) of trichloroacetylchloride. Then, the reaction mixture was agitated at room temperature for 5.5 hours. The thus sedimented crystals were filtered and enough washed with fresh water. Then, the products were recrystallized from benzene to provide 4.8g of trichloroacetyl-N'-3-chlorobenzoylhydrazine in white crystals. m.p.: 143°-144° C. Yield: 76%.

EXAMPLE 2

Preparation of N-chloroacetyl-N'-4-chlorobenzoylhydrazine (Compound No. 3)

22g (0.12 mol) of 4-chlorobenzoic ethyl ether and 6.0g (0.12 mol) of 100%-hydrazine hydrate were added to ethanol, 25 ml, and the reaction mixture was refluxed for 4.5 hours under heat. Upon cooled, the sedimented white crystals were added to ethyl ether and well agitated, pulverized and filtered. Then, the products were agitated well upon further addition with ethyl ether, to provide 8.7g of 4-chlorobenzoic hydrazide in white crystals. m.p.: 162°-164° C. Yield: 43%.

3.4g (0.02 mol) of the hydrazide were then suspended in benzene, 100 ml, and added with 2.0g (0.02 mol) of triethylamine and further droppingly with 3.7g (0.02 mol) of trichloroacetylchloride. The reaction mixture was then agitated for 2.5 hours and the sedimented crystals were filtered and well washed with fresh water to provide 4.4g of N-trichloroacetyl-N'-4-chlorobenzoilhydrazide in white crystals. m.p.: 165°-166° C. Yield: 70%.

EXAMPLE 3

Preparation of N-trichloroacetyl-3,4-dichlorobenzoylhydrazine (Compound No. 6)

17.5g (0.08 mol) of 3,4-dichlorobenzoic ethyl ester and 4.3g (0.086 mol) of 100%-hydrazine hydrate in 30 ml of ethanol were refluxed under heat for 6.5 hours. Upon cooled, the sedimented white crystals were added with ethyl ether and the reaction mixture was enough agitated and pulverized. The thus resulted products were filtered and enough washed with ethyl ether to provide 9.3g of 3,4-dichlorobenzoic hydrazide in white crystals. m.p.: 168°-170° C. Yield: 57%.

The thus obtained hydrazide, 4g (0.02 mol), was suspended in 150 ml of benzene and added with 2.0g (0.02 mol) of triethylamine and further added droppingly with 3.7g (0.02 mol) of trichloroacetylchloride. The reaction mixture was then enough agitated at room temperature for 7 hours and the thus sedimented crystals were filtered and enough washed with fresh water to provide 3.5g of N-trichloroacetyl-N'-3,4-dichlorobenzoic hydrazine in white crystals. m.p.: 183°-185° C. Yield: 50%.

The thus resulted N-trichloroacetyl-N'-chlorobenzoylhydrazine derivatives according to this invention show superior fungicidal effect in relation to various plant disease fungi, especially those of rice blast, tomato late blight and cucumber downy mildew.

Since these novel products do not only contain none of heavy metal atoms which are heavily harmful to human health, but also they present no adverse effect upon cultured plants, thus the fungicidal compositions containing at least one of these novel compounds in its fungicidal amount are highly effective and advantageous for use in the control of various plant diseases.

It is possible to use at least one of the aforementioned novel and effective compounds as the effective and fungicidal component(s) of the compositions of the above kind, and indeed, in any proper state, preferably such as per se, or together with suitable carrier, water, solvent, liquid or extender, and in the form of powder, granules, emulsion, suspension or the like.

The above-novel and fungicidal compounds may be used as per se, or in combination with conventional additives and/or auxiliary agents such as wet extenders, emulsifying solvents and adhesives for more advantageously stabilizing the fungicidal function.

It has been further found that any other agricultural medicines and/or fertilizers may be used in combination with the above novel fungicidal compounds without inviting decomposition or deterioration of the former. These combinedly usable agents may be other fungicides, insecticides and the like. For this purpose, a mixture of these both or concurrent use thereof may be employed, if occasion may desire.

As further examples, several utilization examples will be set forth hereinbelow.

EXAMPLE 4

Application in the form of powder

Compound

N-trichloroacetyl-N'-2-chlorobenzoylhydrazine
(Compound No. 1). m.p.: 168°-170° C.
Agricultural fungicidal composition
Prescription:

the said compound . . . 3 wt. parts
clay . . . 40 wt. parts
talk . . . 57 wt. parts These components are mixed together and pulverized to provide a fine powder which may be dispersed by means of a puffer.

EXAMPLE 5

Application in the form of an aqueous suspension

Compound
N-trichloroacetyl-N'-4-chlorobenzoylhydrazine
(Compound No. 3). m.p.: 165°-166° C.
Agricultural fungicidal composition
Prescription:

the said compound . . . 50 wt. parts
polyoxyethylene alkylaryl ether . . . 6 wt. parts
kieselguhr . . . 44 wt. parts.

These components are mixed together and pulverized and used in the form of an aqueous suspension by addition with a proper amount of water.

In the following, several preferred tests for control of plant diseases.

EXAMPLE 6

Pot Tests for Control of Rice Blast

A large number of porous porcelain pots, each having a diameter of 10 cm, were cultured with "Japonica" - waterfield rice plants of Oryza sativa L,- "variety: SASANISHIKI" of the four leaf stage. Each pot was planted with twenty stems of the rice plant. Three pots consisted a treating area. These plants were well applied with the wettable powder set forth in the foregoing Example 5, upon diluted with ample amount of to desired concentration to provide an aqueous suspension. The suspension was applied onto the plants by means of a liquid spray to such a degree that all the leaves were well wetted. Upon dried, the leaves were inoculated with spores of rice blast fungi, Piricularia oryzae, by spray of an aqueous suspension thereof. Then, the treated pots were placed in high humidity atmosphere at 27°-28° C for four days.

Uppermost leaves of rice plant stems per three pots were precisely reviewed and the observed number of lesions were counted. Equal number of pots having untreated with the fungicidal suspension were equally inoculated as the control, and the number of lesions was counted, and the control rate was found by the following formula.

$$\text{Control rate, \%} = \left(1 - \frac{\text{number of lesions on treated leaves}}{\text{number of lesions on untreated leaves}}\right) \times 100$$

The thus determined results are shown in the following Table II.

Table II

| Compound used | Concentration (ppm) | Number of infected leaf spots | Infection Suppression Rate (%) |
|---|---|---|---|
| No. 1 | 500 | 177 | 77.6 |
| No. 2 | 500 | 15 | 98.1 |
| No. 3 | 500 | 28 | 96.5 |
| No. 4 | 500 | 126 | 84.0 |
| No. 5 | 500 | 0 | 100 |
| No. 6 | 500 | 0 | 100 |
| non-treated | — | 789 | — |

Remarks:
Compound Numbers above shown are same as those set forth in the foregoing Table I.

EXAMPLE 7

Pot test for control of downy mildew on cucumber plants

A number of pots of 10 cm diameter, were used for the culture of cucumber plants of two leaf stage, variety: SAGAMI hampaku. Each plant was planted in a pot. Each three pots were grouped into one treating area. These plants were applied with an aqueous suspension of the wettable powder, Example 5, upon diluted with water. The application was made by means of a liquid spray. Upon dried, all the leaves were inoculated with spores of downy mildew fungi, Pseudoperonospora cubensis, by spraying. Then, the plants were kept in high humidity atmosphere at 22°-23° C for 24 hours, and in a green house for 5 days. After lapse of 5 days upon said inoculation, the degree of infection was determined by consultation with the following classification, as per one leaf per pot and per three pots for each treating area.

Classification

| Index of infection | State of infection |
|---|---|
| "0" | no infection |
| "0.5" | less than 10% infection in terms of inoculated leaf area. |
| "1" | 10 - 20% infection in terms of inoculated leaf area. |
| "2" | 20 - 40% infection in terms of inoculated leaf area. |
| "3" | 40 - 60% infection in terms of inoculated leaf area. |
| "4" | 60 - 80% infection in terms of inoculated leaf area. |
| "5" | over 80% infection in terms of inoculated leaf area. |

The test results are shown in the following Table III.

Table III

| Compound used | Concentration (ppm) | Mean Index of Affection | Chemical Harmful Effect |
|---|---|---|---|
| No. 1 | 500 | 2 | none |
| No. 2 | 500 | 0.5 | none |
| No. 3 | 500 | 0.5 | none |
| No. 4 | 500 | 0.5 | none |
| No. 5 | 500 | 2 | none |
| No. 6 | 500 | 0 | none |
| non-treated | — | 5 | — |

Remarks:
Compound Numbers above shown are same as those set forth in the foregoing Table I.

EXAMPLE 8

Pot test for the control of late blight on tomato plants

A number of pots, each being of 10 cm diameter as before, were planted each with a tomato plant at its four leaf stage, variety being FUKUJU No. 2. Each three pots were grouped into one treating area. The cultured plants were sprayed with an aqueous suspension of the wettable powder as set forth in the foregoing Example 5. An aqueous suspension of spores of tomato late blight fungi, Phytophthora infestans, preparatorily cultured on potato tubers were sprayed over the above treated tomato leaves up